US011780876B2

(12) United States Patent
Zemach

(10) Patent No.: US 11,780,876 B2
(45) Date of Patent: Oct. 10, 2023

(54) METHOD FOR PREPARING A COMPLETE PROTEIN AND USES THEREOF

(71) Applicant: Arthur Merrill Zemach, Durango, CO (US)

(72) Inventor: Arthur Merrill Zemach, Durango, CO (US)

( * ) Notice: Subject to any disclaimer, the term of this patent is extended or adjusted under 35 U.S.C. 154(b) by 763 days.

(21) Appl. No.: 16/250,675

(22) Filed: Jan. 17, 2019

(65) Prior Publication Data

US 2019/0225645 A1 Jul. 25, 2019

Related U.S. Application Data

(60) Provisional application No. 62/617,807, filed on Jan. 16, 2018.

(51) Int. Cl.

| | |
|---|---|
| *C07K 1/00* | (2006.01) |
| *A23L 33/17* | (2016.01) |
| *A23L 33/19* | (2016.01) |
| *A23L 33/175* | (2016.01) |
| *A23L 33/185* | (2016.01) |
| *A23L 33/00* | (2016.01) |
| *A23J 1/12* | (2006.01) |
| *A23J 1/14* | (2006.01) |
| *A23J 1/20* | (2006.01) |
| *A23J 3/16* | (2006.01) |
| *C07K 14/415* | (2006.01) |
| *C07K 14/47* | (2006.01) |
| *A23K 20/147* | (2016.01) |
| *A23K 20/142* | (2016.01) |

(52) U.S. Cl.
CPC ........ *C07K 1/00* (2013.01); *A23J 1/12* (2013.01); *A23J 1/14* (2013.01); *A23J 1/205* (2013.01); *A23J 3/16* (2013.01); *A23L 33/17* (2016.08); *A23L 33/175* (2016.08); *A23L 33/185* (2016.08); *A23L 33/19* (2016.08); *A23L 33/40* (2016.08); *C07K 14/415* (2013.01); *C07K 14/47* (2013.01); *A23K 20/142* (2016.05); *A23K 20/147* (2016.05); *A23V 2002/00* (2013.01)

(58) Field of Classification Search
CPC ...... A23L 33/40; A23L 33/175; A23L 33/185; A23J 1/12; A23J 1/14; A23J 1/205; A23J 3/16

See application file for complete search history.

(56) References Cited

U.S. PATENT DOCUMENTS

| | | |
|---|---|---|
| 4,130,553 A | 12/1978 | Batley et al. |
| 6,241,996 B1 | 6/2001 | Hahn |
| 2009/0018072 A1 | 1/2009 | Scheele |
| 2014/0205710 A1* | 7/2014 | Janow ............ A23L 33/18 426/2 |

FOREIGN PATENT DOCUMENTS

EP 0418593 3/1991

OTHER PUBLICATIONS

"How to Eat Complete Proteins in Vegetarian and Vegan Diets" Nov. 8, 2017 https://integrisok.com/resources/on-your-health/2017/november/how-to-eat-complete-proteins-in-vegetarian-and-vegan-diets (Year: 2017).*
"Protein and Amino Acid Requirements in Human Nutrition" Who Technical Report Series 2007 (Year: 2007).*
Friedman "Nutritional Value of Proteins from Different Food Sources. A Review," Journal of Agricultural and Food Chemistry, Jan. 1996, vol. 44, No. 1, pp. 6-29.
Hsu et al. "The C-PER and T-PER assays for protein quality," Food Technol. Dec. 1978, vol. 32, No. 12, pp. 69-73.
Nishizawa et al. "Protein Quality of High-yielding Rice and Its Improvement by Supplementation of Lysine and Threonine," Agricultural and Biological Chemistry, Feb. 1990, vol. 52, No. 2, pp. 399-406.
International Search Report and Written Opinion for International (PCT) Patent Application No. PCT/EP2019/014024, dated May 22, 2019 14 pages.
International Preliminary Report on Patentability for International (PCT) Patent Application No. PCT/US2019/014024, dated Jul. 30, 2020 8 pages.

* cited by examiner

*Primary Examiner* — Katherine D Leblanc

(57) ABSTRACT

A method of preparing a complete protein by the addition of essential amino acids to an incomplete protein can include calculating an amount of each essential amino acid to be added to an incomplete protein and adding the calculated amount of each essential amino acid to the incomplete protein. The calculations can be done using a particular equation, described herein.

3 Claims, No Drawings

METHOD FOR PREPARING A COMPLETE PROTEIN AND USES THEREOF

CROSS-REFERENCE TO RELATED APPLICATION

This application claims the benefit of priority under 35 U.S.C. § 119(e) to U.S. Provisional Patent Application No. 62/617,807, filed Jan. 16, 2018. The entire disclosure of U.S. Provisional Patent Application No. 62/617,807 is incorporated herein by reference.

FIELD OF INVENTION

The embodiments described herein relate generally to methods for preparing a complete protein and products/compositions made using the complete protein, and more particularly, to a method for preparing a complete protein by the addition of essential amino acids to an incomplete protein.

BACKGROUND OF THE INVENTION

Only complete proteins are used by the human body to repair and build muscle tissue. However, many foods (cow's milk, rice, wheat, etc.) are incomplete proteins, and the portion that is not complete is not used for muscle repair or rebuilding. Rather, the incomplete proteins are burned as fuel or stored as energy.

Dietary proteins that provide all nine indispensable, or essential amino acids (EAAs) are referred to as "complete proteins" (Institute of Medicine (IoM). Dietary reference intakes for energy, carbohydrate, fiber, fat, fatty acids, cholesterol, protein, and amino acids. Washington, D.C.: The National Academies Press. 2005). The World Health Organization (WHO) has published recommendations for the relative amounts of the nine EAAs that comprise a complete protein (Table 1). This definition of a complete protein's EAA composition is based on an adult non-elderly population, and the premise that there are nine EAAs. Such a definition may vary based on the age group being considered, digestibility factors, and if one considers that there are more than nine EAAs. The WHO recommendations from Table 1 are used herein.

TABLE 1

Comparison of Complete Protein (2) and Rice Protein (3)

| Amino Acids | Complete Protein (mg/kg/day) (WHO) | Complete Protein (%) (WHO) | Rice Protein (mg/ 100 g) | Rice Protein (%) | Rice to Complete Protein Ratio |
|---|---|---|---|---|---|
| EAAs | | | | | |
| Histidine | 10 | 5.43% | 1820 | 5.14% | 0.95 |
| Isoleucine | 20 | 10.87% | 3469 | 9.80% | 0.90 |
| Leucine | 39 | 21.20% | 6409 | 18.10% | 0.85 |
| Valine | 26 | 14.13% | 4557 | 12.87% | 0.91 |
| Lysine | 30 | 16.30% | 2420 | 6.84% | 0.42 |
| Methionine + Cysteine | 15 | 8.15% | 3967 | 11.20% | 1.37 |
| Phenylalanine + Tyrosine | 25 | 13.59% | 8673 | 24.50% | 1.80 |
| Threonine | 15 | 8.15% | 2919 | 8.24% | 1.01 |
| Tryptophan | 4 | 2.17% | 1170 | 3.30% | 1.52 |
| TOTAL EAAs | 184 | 100.0% | 35404 | 100.0% | |

TABLE 1-continued

Comparison of Complete Protein (2) and Rice Protein (3)

| Amino Acids | Complete Protein (mg/kg/day) (WHO) | Complete Protein (%) (WHO) | Rice Protein (mg/ 100 g) | Rice Protein (%) | Rice to Complete Protein Ratio |
|---|---|---|---|---|---|
| NEAAs | | | | | |
| Proline | | | 2881 | 6.87% | |
| Serine | | | 3910 | 9.32% | |
| Glycine | | | 3528 | 8.41% | |
| Arginine | | | 6321 | 15.07% | |
| Alanine | | | 4469 | 10.65% | |
| Aspartate | | | 6938 | 16.54% | |
| Glutamic acid | | | 13906 | 33.15% | |
| TOTAL NEAAs | | | 41953 | 100.0% | |
| GRAND TOTAL | | | 77357 | | |

% EAAs = 45.77%
% NEAAs = 54.23%
EAA = essential amino acid; NEAA = non-essential amino acid; WHO = World Health Organization.
(2) = World Health Organization (WHO). Protein and amino acid requirements in human nutrition: report of a joint FAO/WHO/UNU expert consultation. Geneva, Switzerland. 2007.
(3) = Kalman D S. Amino acid composition of an organic brown rice protein concentrate and isolate compared to soy and whey concentrates and isolates. Foods 2014, 3, 394-402; 30 Jun. 2014
[1] The sulfur-containing amino acids, methionine and cysteine, can be converted to one another in the body, although neither of them can be synthesized de novo. Thus they are grouped together in one EAA category. The same is true for the aromatic amino acids, phenylalanine and tryptophan.

Disclosed herein is a method for building or preparing a complete protein from an incomplete dietary protein by adding individual EAAs in appropriate amounts. As disclosed herein a novel mathematical formula has been derived to determine the minimum quantities of each EAA needed to add to an incomplete protein to prepare a complete protein, with no waste. The derived formulas can be applied to incomplete proteins, including but not limited to rice, soy, and whey. In addition, applications to infant formulas, nutritional supplements, meal replacements, and sport nutrition are also disclosed.

SUMMARY OF THE INVENTION

One embodiment of the invention relates to a method for creating a complete protein by the addition of essential amino acids (EAA) to an incomplete protein. In one aspect, the method comprises:

a. calculating the amount of incomplete protein following (Equation 23)

$$D_E = C_E \frac{c_9}{d_9}$$

wherein:
$D_E$ is the EAA component of a dietary protein;
$C_E$ is the amount of complete protein;
$d_9$ is the most prevalent dietary protein EAA, as compared to the corresponding complete protein EAAs;
$c_9$ is the corresponding complete protein EAA to $d_9$;

b. calculating an amount of each EAA to be added to an incomplete protein; and c. adding the calculated amount of each EAA to the incomplete protein, wherein the amount of each EAA to be added is calculated using the following equation (Equation 28):

$$A_i = C_E\left[c_i - d_i\frac{c_9}{d_9}\right]$$

wherein
ci is an amount of amino acid (i) in the amount of engineered complete protein; and
di is an amount of amino acid (i) in the amount of dietary protein.

In one aspect of the method, the dietary protein is selected from the group consisting of rice protein, whey protein, soy protein, and combinations thereof.

In yet another aspect of the method, the EAA is selected from the group consisting of histidine, isoleucine, leucine, valine, lysine, threonine, tryptophan, methionine, cysteine, phenylalanine, and tyrosine.

Another embodiment of the invention relates to a composition comprising (a) a first complete protein portion, comprising: (i) a natural protein component comprising essential and non-essential amino acids; and (ii) an artificial protein component complementary to the natural protein component of (i); and (b) a second complete protein portion, consisting essentially of an artificial protein component.

Another embodiment of the invention relates to a method of producing a composition comprising combining: (a) a natural protein component comprising essential and non-essential amino acids; (b) an artificial protein component complementary to the natural protein component of (a); and (c) a complete protein portion, consisting essentially of an artificial protein component.

In one aspect of the method and/or composition of the invention, the natural protein component is selected from the group consisting of rice protein, whey protein, soy protein, and combinations thereof.

In another aspect of the method and/or composition of the invention, the component complementary to the natural protein component is one or more essential amino acids selected from the group consisting of histidine, isoleucine, leucine, valine, lysine, threonine, tryptophan, methionine, cysteine, phenylalanine, and tyrosine.

In yet another aspect of the method and/or composition of the invention, the artificial protein component is a combination of isolated amino acids.

In one aspect of the method or composition of the invention, the composition further comprises a component selected from the group consisting of carbohydrates, electrolytes, fats, vitamins, and combinations thereof.

In still another aspect of the method and/or composition of the invention, the composition is selected from the group consisting of a food supplement, a sports supplement, and an infant formula.

Another embodiment of the invention relates to a method of producing a composition comprising combining: (a) a natural protein component comprising essential and non-essential amino acids; (b) an artificial protein component complementary to the natural protein component of (a); and (c) a complete protein portion, consisting essentially of an artificial protein component.

DETAILED DESCRIPTION OF THE INVENTION

In the following detailed description of the invention, numerous details, examples, and embodiments of the invention are described. However, it will be clear and apparent to one skilled in the art that the invention is not limited to the embodiments set forth and that the invention can be adapted for any of several applications.

By way of example, some embodiments of the invention include a method for preparing a complete protein by the addition of EAAs to an incomplete protein using a novel mathematical formula, wherein the formula (Equation 17) comprises:

$$D_E = C_E \frac{\left[1 - \sum_{i=1}^{8} c_i\right]}{\left[1 - \sum_{i=1}^{8} d_i\right]}$$

As disclosed herein, Equation 23 (a cleaner version of Equation 17), is the equation of calculating the amount of incomplete dietary protein.

$$D_E = C_E \frac{c_9}{d_9} \qquad \text{(Equation 23)}$$

As further disclosed herein, Equation is the equation for calculating the amount of EAA to be added.

$$A_i = C_E\left[c_i - d_i\frac{c_9}{d_9}\right] \qquad \text{(Equation 28)}$$

Formula Derivation:

A complete protein, by definition, contains only EAAs. Naturally occurring dietary proteins are made up of EAAs and non-indispensable or non-essential amino acids (NEAAs). A dietary protein (D) can be expressed in terms of its EAA and NEAA components:

$$D = D_E + D_N \qquad \text{(Equation 1)}$$

Wherein:
D=Amount of dietary protein
$D_E$=The EAA component of a dietary protein
$D_N$=The NEAA component of a dietary protein The finished product will have to contain some NEAAs, as the NEAAs that are present in most dietary proteins are not removed. The focus on preparing the EAA fraction of the dietary protein to be complete, is as follows:

$$C_E = D_E + A \qquad \text{(Equation 2)}$$

Wherein:
$C_E$=Amount of complete protein
A=Amount of added EAAs

The variables in Equation 2 can be written in terms of their EAA components as:

$$C_E = C_1 + C_2 + C_3 + \ldots + C_9 = \sum_{i=1}^{9} C_i \qquad \text{(Equation 3)}$$

Wherein $C_i$ is the amount of EAA i in complete protein $C_E$ $$D_E = D_1 + D_2 + D_3 + \ldots + D_9 = \sum_{i=1}^{9} C_i \qquad \text{(Equation 4)}$$

Wherein $D_i$ is the amount of EAA i in dietary protein $D_E$ $$A = A_1 + A_2 + A_3 + \ldots + A_9 = \sum_{i=1}^{9} A_i \qquad \text{(Equation 5)}$$

Wherein $A_1$ is the amount of EAA i in the added amino acids A

If $c_i$ is the fraction of $C_E$ that is $C_i$. Then:

$$c_i C_E = C_i \quad \text{(Equation 6)}$$

$$\sum_{i=1}^{9} c_i = 1 \quad \text{(Equation 7)}$$

For the dietary protein:

$$d_i D_E = D_i \quad \text{(Equation 8)}$$

$$\sum_{i=1}^{9} d_i = 1 \quad \text{(Equation 9)}$$

For the added amino acids:

$$a_i A = A_i \quad \text{(Equation 10)}$$

$$\sum_{i=1}^{9} a_i = 1 \quad \text{(Equation 11)}$$

Rearranging Equation 2, and substituting equations 3 and 4, Equation 12 is obtained:

$$A = C_E - D_E = \sum_{i=1}^{9} C_i - \sum_{i=1}^{9} D_i = \sum_{i=1}^{9}[C_i - D_i] \quad \text{(Equation 12)}$$

The goal is to prepare a complete protein from a maximal amount of dietary protein, and a minimal amount of added EAAs. The most prevalent dietary protein EAA is chosen, as compared to the corresponding complete protein EAA, and its amount is set equal to the corresponding amount of complete protein EAA. If for example, the most prevalent dietary protein EAA is designated as number 9, then:

$$D_9 = C_9 \quad \text{(Equation 13)}$$

In this case, the last amino acid will then disappear from the summation in Equation 12, and Equation 14 is obtained:

$$A = \sum_{i=1}^{9}[C_i - D_i] = \sum_{i=1}^{8}[C_i - D_i] \quad \text{(Equation 14)}$$

Equation 14 can be rewritten as follows:

$$A = \sum_{i=1}^{8}[C_i - D_i] = \sum_{i=1}^{8}[c_i C_E - d_i D_E] = C_E \sum_{i=1}^{8} c_i - D_E \sum_{i=1}^{8} d_i \quad \text{Equation (15)}$$

Rearranging Equation 2 to $A = C_E - D_E$ and combining it with Equation 15 results in:

$$C_E - D_E = C_E \sum_{i=1}^{8} c_i - D_E \sum_{i=1}^{8} d_i \quad \text{(Equation 16)}$$

Which rearranges to:

$$D_E = C_E \frac{\left[1 - \sum_{i=1}^{8} c_i\right]}{\left[1 - \sum_{i=1}^{8} d_i\right]} \quad \text{(Equation 17)}$$

Equation 17 can be simplified by replacing the summations over 8 EAA fractions with an expression for the remaining 9th amino acid fraction, as all nine fractions sum to one. For the complete protein:

$$1 = \sum_{i=1}^{9} c_i = \sum_{i=1}^{8} c_i + c_9 \quad \text{(Equation 18)}$$

$$\sum_{i=1}^{8} c_i = 1 - c_9 \quad \text{(Equation 19)}$$

And for the dietary protein:

$$1 = \sum_{i=1}^{9} d_i = \sum_{i=1}^{8} d_i + d_9 \quad \text{(Equation 20)}$$

$$\sum_{i=1}^{8} d_i = 1 - d_9 \quad \text{(Equation 21)}$$

Substituting equations 19 and 21 into Equation 17, Equation 22 is obtained:

$$D_E = C_E \frac{\left[1 - \sum_{i=1}^{8} c_i\right]}{\left[1 - \sum_{i=1}^{8} d_i\right]} = C_E \frac{[1 - (1 - c_9)]}{[1 - (1 - d_9)]} \quad \text{(Equation 22)}$$

Which simplifies to:

$$D_E = C_E \frac{c_9}{d_9} \quad \text{(Equation 23)}$$

If $f_{D_E}$ = The fraction of dietary protein that is EAAs. Then:

$$D_E = f_{D_E} D \quad \text{(Equation 24)}$$

Rearranging Equation 24, and combining with Equation 23, an equation for the amount of dietary protein needed to provide the needed EAA portion is obtained:

$$D = \frac{D_E}{f_{D_E}} = \left[\frac{1}{f_{D_E}}\right] C_E \frac{c_9}{d_9} \quad \text{(Equation 25)}$$

Combining equations 8 and 23, Equation 26 is obtained:

$$D_i = d_i D_E = d_i C_E \frac{c_9}{d_9} \quad \text{(Equation 26)}$$

The amounts of each EAA needed to build or prepare the complete protein is calculated as:

$$A_i = C_i - D_i = c_i C_E - d_i C_E \frac{c_9}{d_9} \quad \text{(Equation 27)}$$

Which simplifies to:

$$A_i = C_E\left[c_i - d_i \frac{c_9}{d_9}\right] \quad \text{(Equation 28)}$$

As described herein, a complete protein can be prepared from an incomplete dietary protein by adding individual EAAs. This allows for the formulation of complete protein components of infant formulas, meal replacements, and sports supplements, based on any given reference protein. The formulas developed herein can work with any number of amino acids in the definition of a reference protein. For example, for low birth weight (LBW) infants, the amino acids arginine, cysteine, glutamine, glycine, proline, taurine, and tyrosine can be considered to be "conditionally indispensable" (Pencharz P B, et al. What are the essential amino acids for the preterm and term infant? In: Bindels J G, et al., eds. Recent Developments in Infant Nutrition. Tenth Nutricia Symposium, vol 9. Springer, Dordrecht, 1996), and a definition of a complete protein for LBW infants can be expanded to include them. In some embodiments, one or more NEAAs are treated in the mathematical framework as EAAs in methods and compositions of the invention. Such compositions are believed to be beneficial because the body of an individual consuming such a material would not have to do as much work interconverting one type of amino acid to another. The mathematical framework presented herein can accommodate reference protein definitions with any number of amino acids.

Compositions described herein comprise a first complete protein portion and a second complete protein portion. The first complete protein portion comprises a natural protein component comprising essential and non-essential amino acids; and an artificial protein component complementary to the natural protein component. The second complete protein portion consists essentially of an artificial protein component. As described herein the term "protein" refers to a composition comprising one or more amino acids.

The complete protein component (comprising the first and second complete protein portions) of a composition of the invention can comprise the first complete protein portion in a range of between about 1 wt. % to about 99 wt. % or any range of whole number wt. % between 1 and 99. Likewise, the second complete protein portion in a range of between about 1 wt. % to about 99 wt. % or any range of whole number wt. % between 1 and 99. In some embodiments, the first complete protein portion is in a range of between about 10 wt. % to about 90 wt. %, 20 wt. % to about 80 wt. %, 30 wt. % to about 80 wt. %, or 40 wt. % to about 60 wt. %. In other embodiments, the second complete protein portion is in a range of between about 10 wt. % to about 90 wt. %, 20 wt. % to about 80 wt. %, 30 wt. % to about 80 wt. %, or 40 wt. % to about 60 wt. %.

In some embodiments, the complete protein component (comprising the first and second complete protein portions) of a composition of the invention can comprise 100 wt. % of the composition, or any range of wt. % between 10 wt. % and 100 wt. %, such as between 20 wt. % and 100 wt. %, between 30 wt. % and 100 wt. %, between 40 wt. % and 100 wt. %, between 50 wt. % and 100 wt. %, between 60 wt. % and 100 wt. %, between 70 wt. % and 100 wt. %, or between 80 wt. % and 100 wt. %.

The first complete protein portion (comprising a natural protein component comprising essential and non-essential amino acids; and an artificial protein component complementary to the natural protein component) can include the natural protein component in a range of from about 10 wt. % to about 99 wt. % or any range of whole numbers between 10 and 99. Similarly, the first complete protein portion can include the artificial protein component in a range of from about 10 wt. % to about 99 wt. % or any range of whole numbers between 10 and 99.

The natural protein component of the compositions described herein can be any naturally occurring protein source, or combinations of protein sources, including without limitation rice protein, whey protein isolate, soy protein, milk protein such as cow's milk protein, Chia seeds, pumpkin seeds, hemp seeds and other seeds, almonds, macadamia nuts and other nuts, lentils, peas, chick peas, and other legumes, mung beans and other beans, seitan, quinoa, wheat, and other grains, and combinations thereof.

The component complementary to the natural protein component is one or more essential amino acids. These essential amino acids are selected from the group consisting of histidine, isoleucine, leucine, valine, lysine, threonine, tryptophan, methionine, cysteine, phenylalanine, tyrosine and combinations thereof.

The artificial protein component of the compositions described herein is a combination of isolated (e.g., pure) amino acids.

The compositions of the present invention can further comprise a component selected from the group consisting of carbohydrates, electrolytes, fats, vitamins, and combinations thereof. In one aspect, when the compositions of the present invention comprise a carbohydrate portion, the ratio of carbohydrate portion to combined first and second complete protein portions can be any suitable amount and, in some embodiments, can be in a ratio that is between about 2:1 and about 5:1 based on weight. For example, the carbohydrate portion to combined first and second complete protein portions can be in a weight ratio of about 2:1, about 3:1, about 4:1 or about 5:1.

In various compositions of the invention, the amount of the complete protein as a weight percentage of total protein is at least about 30%, about 40%, about 50%, about 60%, about 70%, about 80% or about 90% or at least about any whole number greater than 30.

The compositions of the present invention disclosed herein can be a food supplement, a sports supplement, or an infant formula.

A method of the present invention includes producing a composition of the present invention as disclosed herein comprising combining a natural protein component comprising essential and non-essential amino acids; an artificial protein component complementary to the natural protein component; and a complete protein portion, consisting essentially of an artificial protein component.

The following experimental results are provided for purposes of illustration and are not intended to limit the scope of the invention.

EXAMPLE

Example 1

This example describes preparing a complete protein from rice, soy and whey proteins.

The derived formulas disclosed herein, are used to prepare 10 g of complete protein from rice protein and EAAs. The first step is to select a definition of a complete protein, such as the one for non-elderly adults as described by the WHO (World Health Organization (WHO). Protein and amino acid requirements in human nutrition: report of a joint FAO/WHO/UNU expert consultation. Geneva, Switzerland. 2007) in Table 1. Then an amino acid composition analysis is obtained, such as the one provided by Kallman (Kalman D S. Amino acid composition of an organic brown rice protein concentrate and isolate compared to soy and whey concentrates and isolates. Foods 2014, 3, 394-402; 30 Jun. 2014) in Table 1. The percent EAA composition of both complete protein and rice protein is calculated, and then the EAA with the largest ratio of rice protein to complete protein is selected, which is the phenylalanine category. The EAA is designated as number 9, and the EAA portion of rice protein needed is calculated by:

$$D_E = C_E \frac{c_9}{d_9} = (10 \text{ g}) \frac{0.136}{0.245} = 5.55 \text{ g} \qquad \text{(Equation 23)}$$

Next, the amounts of each EAA to add is calculated as follows:

$$A_i = C_E \left[ c_i - d_i \frac{c_9}{d_9} \right] = (10 \text{ g}) \left[ c_i - d_i \frac{0.136}{0.245} \right] \qquad \text{(Equation 28)}$$

Results for each EAA are given in Table 2.

TABLE 2

Construction of a Complete Protein from Rice Protein and EAAs

| EAA | Complete Protein (%) (WHO) | Rice Protein (%) | Rice to Reference Ratio | Complete Protein (g) | EAA Component of Rice Protein (g) | Added EAAs (g) |
|---|---|---|---|---|---|---|
| Histidine | 5.43% | 5.14% | 0.95 | 0.543 | 0.285 | 0.258 |
| Isoleucine | 10.87% | 9.80% | 0.90 | 1.087 | 0.543 | 0.544 |
| Leucine | 21.20% | 18.10% | 0.85 | 2.120 | 1.004 | 1.116 |
| Valine | 14.13% | 12.87% | 0.91 | 1.413 | 0.714 | 0.699 |
| Lysine | 16.30% | 6.84% | 0.42 | 1.630 | 0.379 | 1.251 |
| Methionine + Cysteine | 8.15% | 11.20% | 1.37 | 0.815 | 0.621 | 0.194 |
| Phenylalanine + Tyrosine | 13.59% | 24.50% | 1.80 | 1.359 | 1.359 | 0.000 |
| Threonine | 8.15% | 8.24% | 1.01 | 0.815 | 0.457 | 0.358 |
| Tryptophan | 2.17% | 3.30% | 1.52 | 0.217 | 0.183 | 0.034 |
| TOTALS | 100.0% | 100.0% | | 10.00 | 5.55 | 4.45 |

EAA = essential amino acid;
NEAA = non-essential amino acid;
WHO = World Health Organization.

From Table 1 the rice protein is 45.77% EAAs. The amount of rice protein needed to provide 5.55 g of EAA portion is:

$$D = \frac{D_E}{f_{D_E}} = \frac{(5.55 \text{ g})}{0.4577} = 12.12 \text{ g} \quad \text{(Equation 25)}$$

Therefore, 10 g of complete protein can be built up or prepared from 12.12 g rice protein, plus 0.26 g histidine, 0.54 g isoleucine, 1.12 g leucine, 0.70 g valine, 1.25 g lysine, 0.19 g methionine, 0 g phenylalanine, 0.36 g threonine, and 0.03 g tryptophan.

Corresponding calculations can be performed for soy and whey proteins. Their EAA compositions are given in Tables 3 and 5, and the results of the calculations in Tables 4 and 6. For soy protein, the phenylalanine category has the largest (dietary protein)/(complete protein) ratio. 10 g of complete protein can be built up or prepared from 15.31 g of soy protein, plus 0.14 g histidine, 0.35 g isoleucine, 0.94 g leucine, 0.70 g valine, 0.70 g lysine, 0.44 g methionine, 0 g phenylalanine, 0.27 g threonine, 0.02 g tryptophan.

For whey protein, the EAA with the largest (dietary protein)/(complete protein) ratio is threonine. 10 g of complete protein can be built up or prepared from 10.27 g of whey protein, plus 0.41 g histidine, 0.51 g isoleucine, 1.06 g leucine, 0.81 g valine, 0.63 g lysine, 0.43 g methionine, 0.82 g phenylalanine, 0 g threonine, 0.02 g tryptophan.

TABLE 3

Comparison of WHO EAA Goals (2) and Soy Protein (3)

| Amino Acids | Complete Protein (mg/kg/day) (WHO) | Complete Protein (%) (WHO) | Soy Protein (mg/ 100 g) | Soy Protein (%) | Soy to Complete Protein Ratio |
|---|---|---|---|---|---|
| EAAs | | | | | |
| Histidine | 10 | 5.43% | 2303 | 6.22% | 1.15 |
| Isoleucine | 20 | 10.87% | 4253 | 11.49% | 1.06 |
| Leucine | 39 | 21.20% | 6783 | 18.33% | 0.86 |
| Valine | 26 | 14.13% | 4098 | 11.07% | 0.78 |
| Lysine | 30 | 16.30% | 5327 | 14.39% | 0.88 |
| Methionine + Cysteine | 15 | 8.15% | 2176 | 5.88% | 0.72 |
| Phenylalanine + Tyrosine | 25 | 13.59% | 7815 | 21.12% | 1.55 |
| Threonine | 15 | 8.15% | 3137 | 8.48% | 1.04 |
| Tryptophan | 4 | 2.17% | 1116 | 3.02% | 1.39 |
| TOTAL EAAs | 184 | 100.0% | 37008 | 100.0% | |
| NEAAs | | | | | |
| Proline | | | 4960 | 9.71% | |
| Serine | | | 4593 | 8.99% | |
| Glycine | | | 3603 | 7.06% | |
| Arginine | | | 6670 | 13.06% | |
| Alanine | | | 3589 | 7.03% | |
| Aspartate | | | 10203 | 19.98% | |
| Glutamic acid | | | 17452 | 34.17% | |
| TOTAL NEAAs | | | 51070 | 100.0% | |
| GRAND TOTAL | | | 88078 | | |

% EAAs = 42.02%
% NEAAs = 57.98%

EAA = essential amino acid; NEAA = non-essential amino acid; WHO = World Health Organization.
(2) = World Health Organization (WHO). Protein and amino acid requirements in human nutrition: report of a joint FAO/WHO/UNU expert consultation. Geneva, Switzerland. 2007.
(3) = Kalman D S. Amino acid composition of an organic brown rice protein concentrate and isolate compared to soy and whey concentrates and isolates. Foods 2014, 3, 394-402; 30 Jun. 2014
[1] The sulfur-containing amino acids, methionine and cysteine, can be converted to one another in the body, although neither of them can be synthesized de novo. Thus they are grouped together in one EAA category. The same is true for the aromatic amino acids, phenylalanine and tryptophan.

TABLE 4

Construction of a Complete Protein from Soy Protein and EAAs

| EAA | Complete Protein (%) (WHO) | Soy Protein (%) | Soy to Reference Ratio | Complete Protein (g) | EAA Component of Soy Protein (g) | Added EAAs (g) |
|---|---|---|---|---|---|---|
| Histidine | 5.43% | 6.22% | 1.15 | 0.543 | 0.400 | 0.143 |
| Isoleucine | 10.87% | 11.49% | 1.06 | 1.087 | 0.739 | 0.348 |
| Leucine | 21.20% | 18.33% | 0.86 | 2.120 | 1.179 | 0.940 |
| Valine | 14.13% | 11.07% | 0.78 | 1.413 | 0.712 | 0.701 |
| Lysine | 16.30% | 14.39% | 0.88 | 1.630 | 0.926 | 0.704 |
| Methionine + Cysteine | 8.15% | 5.88% | 0.72 | 0.815 | 0.378 | 0.437 |
| Phenylalanine + Tyrosine | 13.59% | 21.12% | 1.55 | 1.359 | 1.359 | 0.000 |
| Threonine | 8.15% | 8.48% | 1.04 | 0.815 | 0.545 | 0.270 |
| Tryptophan | 2.17% | 3.02% | 1.39 | 0.217 | 0.194 | 0.023 |
| TOTALS | 100.0% | 100.0% |  | 10.00 | 6.43 | 3.57 |

EAA = essential amino acid;
NEAA = non-essential amino acid;
WHO = World Health Organization.

TABLE 5

Comparison of WHO EAA Goals (2) and Whey Protein (3)

| Amino Acids | Complete Protein (mg/kg/day) (WHO) | Complete Protein (%) (WHO) | Whey Protein (mg/100 g) | Whey Protein (%) | Whey to Complete Protein Ratio |
|---|---|---|---|---|---|
| EAAs |  |  |  |  |  |
| Histidine | 10 | 5.43% | 1311 | 2.54% | 0.47 |
| Isoleucine | 20 | 10.87% | 5600 | 10.86% | 1.00 |
| Leucine | 39 | 21.20% | 10239 | 19.86% | 0.94 |
| Valine | 26 | 14.13% | 5879 | 11.40% | 0.81 |
| Lysine | 30 | 16.30% | 9700 | 18.81% | 1.15 |
| Methionine + Cysteine | 15 | 8.15% | 3778 | 7.33% | 0.90 |
| Phenylalanine + Tyrosine | 25 | 13.59% | 5258 | 10.20% | 0.75 |
| Threonine | 15 | 8.15% | 7911 | 15.34% | 1.88 |
| Tryptophan | 4 | 2.17% | 1889 | 3.66% | 1.69 |
| TOTAL EAAs | 184 | 100.0% | 51565 | 100.0% |  |
| NEAAs |  |  |  |  |  |
| Proline |  |  | 5739 | 11.92% |  |
| Serine |  |  | 4921 | 10.22% |  |
| Glycine |  |  | 1421 | 2.95% |  |
| Arginine |  |  | 1779 | 3.70% |  |
| Alanine |  |  | 4800 | 9.97% |  |
| Aspartate |  |  | 10161 | 21.11% |  |
| Glutamic acid |  |  | 19311 | 40.12% |  |
| TOTAL NEAAs |  |  | 48132 | 100.0% |  |
| GRAND TOTAL |  |  | 99697 |  |  |

% EAAs = 51.72%
% NEAAs = 48.28%

EAA = essential amino acid; NEAA = non-essential amino acid; WHO = World Health Organization.
(2) = World Health Organization (WHO). Protein and amino acid requirements in human nutrition: report of a joint FAO/WHO/UNU expert consultation. Geneva, Switzerland. 2007.
(3) = Kalman D S. Amino acid composition of an organic brown rice protein concentrate and isolate compared to soy and whey concentrates and isolates. Foods 2014, 3, 394-402; 30 Jun. 2014
[1] The sulfur-containing amino acids, methionine and cysteine, can be converted to one another in the body, although neither of them can be synthesized de novo. Thus they are grouped together in one EAA category. The same is true for the aromatic amino acids, phenylalanine and tryptophan.

TABLE 6

Construction of a Complete Protein from Whey Protein and EAAs

| EAA | Complete Protein (%) (WHO) | Whey Protein (%) | Whey to Reference Ratio | Complete Protein (g) | EAA Component of Whey Protein (g) | Added EAAs (g) |
|---|---|---|---|---|---|---|
| Histidine | 5.43% | 2.54% | 0.47 | 0.543 | 0.135 | 0.408 |
| Isoleucine | 10.87% | 10.86% | 1.00 | 1.087 | 0.577 | 0.510 |
| Leucine | 21.20% | 19.86% | 0.94 | 2.120 | 1.055 | 1.064 |
| Valine | 14.13% | 11.40% | 0.81 | 1.413 | 0.606 | 0.807 |
| Lysine | 16.30% | 18.81% | 1.15 | 1.630 | 1.000 | 0.631 |
| Methionine + Cysteine | 8.15% | 7.33% | 0.90 | 0.815 | 0.389 | 0.426 |
| Phenylalanine + Tyrosine | 13.59% | 10.20% | 0.75 | 1.359 | 0.542 | 0.817 |

TABLE 6-continued

Construction of a Complete Protein from Whey Protein and EAAs

| EAA | Complete Protein (%) (WHO) | Whey Protein (%) | Whey to Reference Ratio | Complete Protein (g) | EAA Component of Whey Protein (g) | Added EAAs (g) |
|---|---|---|---|---|---|---|
| Threonine | 8.15% | 15.34% | 1.88 | 0.815 | 0.815 | 0.000 |
| Tryptophan | 2.17% | 3.66% | 1.69 | 0.217 | 0.195 | 0.023 |
| TOTALS | 100.0% | 100.0% | | 10.00 | 5.31 | 4.69 |

EAA = essential amino acid;
NEAA = non-essential amino acid;
WHO = World Health Organization.

Abbreviations

EAA=essential amino acid; NEAA=non-essential amino acid; WHO=World Health Organization

REFERENCES

1. Institute of Medicine (IoM). Dietary reference intakes for energy, carbohydrate, fiber, fat, fatty acids, cholesterol, protein, and amino acids. Washington, D.C.: The National Academies Press. 2005. Internet: doi.org/10.17226/10490 (accessed 28 Dec. 2018).
2. World Health Organization (WHO). Protein and amino acid requirements in human nutrition: report of a joint FAO/WHO/UNU expert consultation. Geneva, Switzerland. 2007. Internet: www.who.int/iris/handle/10665/43411 (accessed 28 Dec. 2018).
3. Kalman D S. Amino acid composition of an organic brown rice protein concentrate and isolate compared to soy and whey concentrates and isolates. Foods 2014, 3, 394-402; 30 Jun. 2014 Internet: www.mdpi.com/2304-8158/3/3/394/htm (accessed 5 Jan. 2019).
4. Pencharz P B, House J D, Wykes L J, Ball R O. What are the essential amino acids for the preterm and term infant? In: Bindels J G, Goedhart A C, Visser H K A, eds. Recent Developments in Infant Nutrition. Tenth Nutricia Symposium, vol 9. Springer, Dordrecht, 1996.

What is claimed:

1. A method for preparing a complete protein, with no waste, by the addition of essential amino acids (EAA) to an incomplete protein, the method comprising:

a. calculating the amount of incomplete protein following (Equation 23)

$$D_E = C_E \frac{c_9}{d_9}$$

wherein:
   $D_E$ is the EAA component of a dietary protein;
   $C_E$ is the amount of complete protein;
   $d_9$ is the most prevalent dietary protein EAA, as compared to the corresponding complete protein EAAs;
   $c_9$ is the corresponding complete protein EAA to $d_9$, b. calculating an amount of each EAA to be added to the incomplete protein; and
   c. adding the calculated amount of each EAA to the incomplete protein, wherein the amount of each EAA to be added is calculated using the following equation (Equation 28):

$$A_E = C_E \left[ c_i - d_i \frac{c_9}{d_9} \right]$$

wherein:
   $c_i$ is an amount of amino acid (i) in the amount of engineered complete protein; and $d_i$ is an amount of amino acid (i) in the amount of dietary protein.

2. The method of claim 1, wherein the dietary protein is selected from the group consisting of rice protein, whey protein, soy protein, and combinations thereof.

3. The method of claim 1, wherein the EAA is selected from the group consisting of histidine, isoleucine, leucine, valine, lysine, threonine, tryptophan, methionine, cysteine, phenylalanine, and tyrosine.

* * * * *